United States Patent [19]
Nakatsugawa

[11] 4,432,348
[45] Feb. 21, 1984

[54] ENHANCER OF ANTI-TUMOR EFFECT

[75] Inventor: Shigekazu Nakatsugawa, Kyoto, Japan

[73] Assignee: Yamasa Shoyu Kabushiki Kaisha, Japan

[21] Appl. No.: 300,977

[22] Filed: Sep. 9, 1981

[30] Foreign Application Priority Data

Sep. 17, 1980 [JP] Japan .................................. 55-128001

[51] Int. Cl.³ ............................................ A61K 31/505
[52] U.S. Cl. .................................... 128/1.1; 424/180
[58] Field of Search ................... 424/180; 536/23, 29; 128/1.1

[56] References Cited

U.S. PATENT DOCUMENTS 3,622,561 11/1971 Robins ............................ 424/180 X
3,919,193 11/1975 Mian et al. ...................... 424/180 X
4,144,329 3/1979 Umezawa et al. .................. 424/181
4,177,348 12/1979 Shealy et al. ................... 424/180 X Primary Examiner—George F. Lesmes
Assistant Examiner—Nancy A. B. Swisher
Attorney, Agent, or Firm—Wenderoth, Lind & Ponack

[57] ABSTRACT

A nucleotide selected from the group consisting of 3'-deoxyguanosine-5'-monophosphate, 3'-deoxyadenosine-5'-monophosphate and pharmaceutically-acceptable salts thereof enhances, when administered to a tumor-bearing animal under an anti-tumor treatment, the anti-tumor effect due to the anti-tumor treatment. The anti-tumor treatment comprises irradiation of a tumor site of the animal or administration of an anti-tumor agent to the animal.

12 Claims, No Drawings

ENHANCER OF ANTI-TUMOR EFFECT

BACKGROUND OF THE INVENTION

1. Field of the Art

This invention relates to an enhancer of anti-tumor effect.

In the art of treatment of tumors, there have been many developments from various aspects. In radiotherapy, as a branch of the development, there have also been attempts to improve the results of therapy. As one method, it is proposed to improve geometrical distribution by use of such methods as radiation of accelerated heavy ion particles or $\pi$ mesons. Another approach now under the development is to enhance selectively the sensitivity of tumor cells under hypoxic conditions, which are most resistant to radiotherapy among tumors, by utilizing a hypoxic cell sensitizer. Alternatively, combination treatments incorporating a method utilizing other anti-tumor factors, such as hyperthermia or chemotherapy have been attempted.

However, in the method for improvement of geometrical dose distribution, it is required to use enormous funds for installation of an accelerator and auxiliary equipment necessary for practicing the method as well as a large personnel requirements, including expert engineers and physicians. Other methods also involve drawbacks such as great damage to normal cells. For example, misonidazole, which is a hypoxic cell sensitizer, has neurotoxicity, and hence it is difficult to administer it in a large quantity, whereby no great radiosensitizing effect can be expected at concentrations available in clinical use, its effect being small in a low dose range (less than 1000 rad) as employed in a routine therapy.

In view of the fact that the tumor cells with radioresistance under hypoxic conditions are at a quiescent stage, I have investigated the possibility of radiosensitization by inhibiting potentially lethal damage repair (hereinafter referred to as "PLDR"), which is especially marked in quiescent cells. During the course of this investigation, 3'-deoxyadenosine (cordycepin, herein referred to as "3'-dAdo") was confirmed to have a PLDR-inhibiting ability. However, 3'-dAdo is readily inactivated by adenosinedeaminase in bodies. I found that the PLDR-inhibiting ability of 3'-dAdo can be strengthened and prolonged by using it in combination with 2'-deoxycoformycin, which is an inhibitor against adenosinedeaminase. However, there is also a report that 2'-deoxycoformycin may cause damage to the immune systems, and 3'-dAdo is also known to have various side effects. Thus, it would be very desirable to have a radiosensitizing substance which is more stable, lower in toxicity, and more effective than 3'-dAdo.

On the other hand, in the field of chemotherapy of tumors, multiple anti-tumor agents have been combined to be used for the following purposes and effects:

(1) By using in combination a number of different agents selected from those of alkylating agents, antimetabolites, antibiotics and alkaloids, which show mutually no cross resistance and are different in mechanism of action, the anti-tumor effect can be enhanced additively or synergistically against tumors which are composed of a mixture of tumor cells different in sensitivity to various agents.

(2) By using in combination anti-tumor agents different in the way they attack tumor cells which are proliferating at random, various stages in the cell cycle of tumor cells can be widely attacked to ensure complete killing of tumor cells.

(3) By using not only agents different in mechanism of action but also those having relatively similar mechanisms of action, a synergistic effect can be expected. For example, by using in combination a number of agents which are blocking a series of steps participating in DNA synthesis, a strong synergistic effect can be exhibited.

(4) Each anti-tumor agent has its specific side effect. Thus, by using in combination a number of agents with different side effects each in a dosage less than the limit above which side effects appear, the anti-tumor effect can be expected to be increased additively or synergistically while the side effects are dispersed.

By such a multi-agent combination treatment, it has been made possible to obtain an effect which could not be produced by using a single anti-tumor agent. However, each of the agents used in combination in such an application is an anti-tumor agent which can be independently used.

There have also been various attempts to use in combination with an anti-tumor agent a compound which does not per se have an anti-tumor effect for the purpose of strengthening the effect of the anti-tumor agent by preventing the anti-tumor agent from being inactivated in bodies. For example, it is known to use cytidine or uridine in combination with 1-$\beta$-D-arabinofuranosylcytosine (hereinafter referred to as "araC"), as disclosed in Japanese Laid-Open Patent Application No. 24150/1980. It is also known to use tetrahydrouridine, which is an inhibitor against cytidinedeaminase, in combination with araC, as disclosed in Cancer Research Vol.30, p. 2166–2172, 1970. Further, there is known another method wherein 5-fluorouracil (hereinafter referred to as "5-FU") or a derivative thereof is combined with a pyrimidine compound such as, for example, uracil, cytosine, thymine, orotic acid, 5-bromouracil, 5-iodouracil, 1-acetyluracil, 1-(2-tetrahydrofuryl)-uracil, 3-benzoyluracil, 1-cyclohexycarbamoyluracil, 1-n-hexycarbamoyluracyl, uridine, 2'-deoxyuridine, 5-bromo-2'-deoxyuridine, cytidine, or 2'-deoxycytidine.

With respect to a chemotherapeutics such as Bleomycin (hereinafter referred to as "BLM") or 5-FU, PLDR is also recognized similarly as in the case of radiotherapy, as reported in the Journal of the National Cancer Institute, Vol.50, No.2, p.529–533, 1973.

SUMMARY OF THE INVENTION

In view of the above described state of the art, I have made extensive studies with the aim of obtaining a radiosensitizing agent having a PLDR-inhibiting activity with low toxicity and good stability. As a result, it has now been found that 3'-deoxyguanosine-5'-monophosphate and 3'-deoxyadenosine-5'-monophosphate, in addition to 3'-dAdo, have excellent radiosensitizing activities. I have also found that these 3'-deoxynucleotides can also exhibit excellent effect in strengthening anti-tumor effect in treatment of malignant tumors by chemotherapy. These findings have led to the development of the present invention. Thus, the present invention provides a method and a pharmaceutical agent to be used for strengthening the anti-tumor effect in treatment of malignant tumors by irradiation and/or an anti-tumor agent.

In one of its aspects, the present invention relates to a method for enhancement of anti-tumor effect, which comprises administering to a tumor-bearing animal under the anti-tumor treatment an enhancer of anti-tumor effect selected from the group consisting of 3'-deoxyguanosine-5'-monophosphate, 3'-deoxyadenosine-5'-monophosphate and pharmaceutically-acceptable salts thereof.

The term "animal" as herein used means a human being or a lower animal.

The wording "under the anti-tumor treatment" means the state where a tumor-bearing animal is being subjected to physical, chemical or physicochemical treatment for suppressing tumors or where there is retained in that animal an influence due to such a treatment. Accordingly and more specifically, the enhancer is administered to the animal before, simultaneously with, or after irradiation when the anti-tumor treatment comprises irradiation to a tumor site of the animal. The enhancer is administered before, simultaneously with, or after administration of an anti-tumor agent when the anti-tumor treatment comprises administration of an anti-tumor agent.

In another aspect of the present invention, it relates to a method for therapy of tumors, which comprises administering to a tumor-bearing animal under the anti-tumor treatment an enhancer of anti-tumor effect selected from the aforesaid group.

In still another aspect thereof, the present invention relates to an enhancer of anti-tumor effect, comprising an enhancer of anti-tumor effect selected from the aforesaid group and a pharmaceutically acceptable carrier.

In a further aspect thereof, the present invention relates to a chemotherapeutic composition for treating tumors, comprising an anti-tumor agent, an enhancer of anti-tumor effect selected from the aforesaid group, and a pharmaceutically acceptable carrier.

The enhancer is administered to a tumor-bearing animal under the anti-tumor treatment in accordance with the present invention and the anti-tumor effect due to the anti-tumor treatment is significantly enhanced as evidenced by the data set forth in the following experiments.

DETAILED DESCRIPTION OF THE INVENTION

Enhancers

The enhancer in accordance with the present invention is selected from the group consisting of 3'-deoxyguanosine-5'-monophosphate, hereinafter referred to as 3'-dGuo-5'-MP, 3'-deoxyadenosine-5'-monophosphate, hereinafter referred to as 3'-dAdo-5'-MP, and pharmaceutically-acceptable salts thereof. Examples of the pharmaceutically-acceptable salts are their alkali metal (e.g., sodium, potassium, lithium) salts, alkaline earth metal (e.g., calcium, magnesium) salts and ammonium salts. These can of course be used in combination with each other or with other radiosensitizers or enhancers of chemotherapy.

Enhancement of anti-tumor effect

The pharmaceutical agent according to the present invention may be used for the purpose of enhancing the anti-tumor effect in the treatment of a malignant tumor, for which radiotherapy or chemotherapy by anti-tumor agents is to be applied, in combination with the treatments by these therapeutical methods.

In the case where the pharmaceutical agent of the present invention is used as a radiosensitizing agent for the purpose of enhancing the effect of radiotherapy, it may be administered before or after exposure, or even during exposure, if the occasion permits it, to the irradiation in radiotherapy. As to radiotherapy per se, the use of specific method and conditions is not required, but conventional radiotherapy techniques may be employed. By the use of the enhancer of the present invention in combination, it has become possible to apply radiotherapy with irradiation in the region of lower dosage than in the prior art. As the ionizing radiations for radiotherapy, those generally employed such as X-rays, lineac high energy X-rays, betatron 32 MeV electron beams or $^{a}Co\gamma$-rays may be used.

When used for the purpose of enhancing the anti-tumor effect in chemotherapy by an anti-tumor agent, the enhancer of the present invention may be administered simultaneously with, or after or before administration of the anti-tumor agent. As anti-tumor agents whose anti-tumor effect can be enhanced by the enhancer of the present invention, various kinds of agents, including those having activity similar to ionizing radiations as well as those having PLDR activity may be mentioned. Examples of anti-metabolites include Methotrexate; 6-mercaptopurine; 5-FU and its derivatives, such as, for example, 5-fluorouridine, 5-fluoro-2'-deoxyuridine, 1-$\beta$-D-arabinofuranosyl-5-fluorocytosine, 1-(2-tetrahydrofuryl)-5-fluorouracil, 1-(n-hexylcarbamoyl)-5-fluorouracil, 1-ethoxymethyl-5-fluorouracil, 1-ethoxycarbonyl-5-fluorouracil, and b 5-fluoro-5'-deoxyuridine; and araC and its derivatives, such as, for example, cyclocytidine, $N^4$-palmitoyl araC, $N^4$-stearoyl araC, $N^4$-behenoyl araC, araC-5'-stearylphosphate, and araC-5'-oleylphosphate may be mentioned. Examples of anti-tumor antibiotics include BLM; Neocarzinostatin; and Anthracycline type antibiotics, such as, for example, Daunomycin, Adriamycin, and Aclacinomycin. Examples of alkylating agents include nitrosourea, such as, for example, ACNU, BCNU, CCNU, MCCNU; 3'-[3-(2-chloroethyl)-3-nitrosoureido]-3'-deoxythymidine; and 3'-(3-methyl-3-nitrosoureido)-3'-deoxythymidine. These anti-tumor agents may be administered by any method and in any dosage, which are not specifically limited in combination with the enhancer of the present invention, but optimum conditions may suitably be selected for each agent used.

The method for administration of the enhancer of the present invention may be either systemic administration or local administration. Various dosages unit forms can be selected depending on the purposes of therapy and the methods of administration. For example, as the forms for systemic administration, an oral administration form such as tablet, capsule, granule or solution, or a non-oral administration form such as injection, suppository, etc., can be used. On the other hand, as a local administration form, a slow-releasing-capsule, an ointment or an injection can be used. In the preparing of such as dosage unit form, it is possible to make a preparation according to a conventional method using a pharmaceutically acceptable carrier. Various modifications in preparation suitable for the object of the present invention may also be utilized. Further, as one embodiment of an enhancer of anti-tumor agent according to this invention, the anti-tumor agent to be used in combination and the active ingredient in the present pharmaceutical agent may be formulated into a combined drug of the same dosage form. The compositions of the components in such a formulation may suitably be determined depending on the components employed.

As mentioned above, the enhancer of the present invention can be administered simultaneously with administration of an anti-tumor agent. In such a case, instead of administering both chemicals separately, they can be administered in the form of one formulation.

The enhancer in accordance with the present invention can be used when the animal is under the anti-tumor treatment comprising both administration of an anti-tumor agent and irradiation.

The enhancer of the present invention is used in an amount effective for enhancement of anti-tumor activity. More specifically, the dosage of the pharmaceutical agent of the present invention per day, which may slightly differ depending on the active ingredient employed, in general, is desirably 20 to 3,000 mg for an oraladministration, 0.5 to 500 mg for an injection, and 20 to 2,000 mg for a suppository, as determined from basic experiments on anti-tumor effectiveness. The optimum effective amount should be determined by judgement of a physician according to the irradiation used, its dosage, the anti-tumor agent used, its dosage, the conditions of disease, the affected part, etc.

The pharmacological effects of the pharmaceutical agents of the present invention are shown below with data from the tests of radiosensitizing effect thereof.

EXPERIMENT 1

Radiosensitizing effect on the experimental tumors in mice

EMT-6 tumor cells ($2 \times 10^5$) were inoculated intradermally into the right thighs of BALB/c-strain female mice (8 weeks old, 6 or more mice for each group). When the tumor size reached 6 to 7 mm in diameter after inoculation of the tumor cells, local irradiation with a 32 MeV electron beam was carried out at 1,500 rad under no anesthesia and thereafter 3'-dGuo-5'-MP and 3'-dAdo-5'-MP dissolved in physiological saline solution, was administered intraperitoneally to each mouse in the indicated doses of respective agents. After these treatments, the tumor sizes were measured in tri-dimensional diameters every day or every other day for 28 days, and compared with the control group with respect to the following items:

$$\text{Mean tumor diameter} = \left( \frac{\text{Maximum longitudinal diameter} + \text{Maximum lateral diameter} + \text{Maximum height (diameter)}}{3} \right) \quad (1)$$

$$\text{Diameter ratio} = \frac{\text{Mean tumor diameter}}{\text{Mean tumor diameter at the time of irradiation}} \quad (2)$$

$$\text{Volume ratio} = (\text{Diameter ratio})^3 \quad (3)$$

The results are shown in Table 1 and Table 2, in which "cure" means that the tumors completely vanished during the observation period.

TABLE 1

Sensitizing effect of enhancer on X-ray therapy of EMT-6 tumors

| Treatment | Mean tumor diameter at the time of irradiation (mm) | 2 weeks after treatment | | | 3 weeks after treatment | | |
|---|---|---|---|---|---|---|---|
| | | Mean tumor diameter (mm) | Diameter ratio | Volume ratio | Mean tumor diameter (mm) | Diameter ratio | Volume ratio |
| Irradiation (1500 rad) alone (n = 10) | 6.80 ± 0.31 | 7.41 ± 0.51 | 1.09 ± 0.07 | 1.44 ± 0.23 | 0.29 ± 0.83 | 1.17 ± 0.13 | 2.06 ± 0.30 |
| Irradiation + 3'-dGuo-5'-MP (100 mg/kg) (n = 9) | 6.46 ± 0.23 | 6.17 ± 0.90 | 0.93 ± 0.13 | 1.19 ± 0.32 | 5.95 ± 1.22 | 0.90 ± 0.18 | 1.45 ± 0.46 |
| Irradiation + 3'-dAdo-5'-MP (75 mg/kg) (n = 10) | 7.07 ± 0.23 | 4.75 ± 1.06 | 0.66 ± 0.14 | 0.63 ± 0.18 | 3.65 ± 1.24 | 0.49 ± 0.17 | 0.58 ± 0.27 |

TABLE 2

Sensitizing effect of enhancer on X-ray radiation on EMT-6 tumors (on the 28th day after treatment)

| Treatment | Cure | Less than 0.5 of volume ratio excluding cure; Tumor regression rate: rapid | 0.5 to less than 1 of volume ratio excluding cure; Tumor regression rate: slow | 1.0 to less than 2.0 of volume ratio excluding cure; regrowth: slow | 2.0 or more of volume ratio excluding cure; regrowth: rapid |
|---|---|---|---|---|---|
| Irradiation (1500 rad) alone | 1/10 (10%) | 0/10 (0%) | 0/10 (0%) | 3/10 (30%) | 6/10 (60%) |
| Irradiation + 3'-dGuo-5'-MP (100 mg/kg) | 2/9 (22%) | 0/9 (0%) | 2/9 (22%) | 5/9 (56%) | 0/9 (0%) |
| Irradiation + 3'-dAdo-5'-MP | 5/10 (50%) | 2/10 (20%) | 0/10 (0%) | 2/10 (20%) | 1/10 (10%) |

TABLE 2-continued

| | | Sensitizing effect of enhancer on X-ray radiation on EMT-6 tumors (on the 28th day after treatment) | | | |
|---|---|---|---|---|---|
| Treatment | Cure | Less than 0.5 of volume ratio excluding cure; Tumor regression rate: rapid | 0.5 to less than 1 of volume ratio excluding cure; Tumor regression rate: slow | 1.0 to less than 2.0 of volume ratio excluding cure; regrowth: slow | 2.0 or more of volume ratio excluding cure; regrowth: rapid |
| (75 mg/kg) | | | | | |

EXPERIMENT 2

Enhancement of the effect of anti-tumor agents on the experimental tumors in mice EMT-6 tumor cells ($1 \times 10^6$) were inoculated intradermally into the right thighs of BALB/c-strain female mice (8 weeks old). On the 11th day after inoculation of the tumor cells and thereafter, 3'-dGuo-5'-MP in physiological saline solutions were administered intraperitoneally to the mice for 8 consecutive days in the dose of 50 mg/kg. The pharmaceutical agents of the present invention were administered an hour after administration of araC. After commencement of the treatment with pharmaceutical agents, the tumor sizes were measured and compared with the control group.

The results are given in Table 3.

TABLE 3

| | | Mean tumor diameter mm (ratio) | | | |
|---|---|---|---|---|---|
| Treatment with anti-tumor agents | Treatment with the enhancer of the invention | Immediately before treatment | 7 days after commencement of treatment | 14 days after commencement of treatment | 21 days after commencement of treatment |
| Control (n = 9) | — | 7.51 ± 0.53 | 10.07 ± 0.99 (1.34 ± 0.14) | 12.40 ± 1.36 (1.66 ± 0.21) | 16.18 ± 1.34 (2.16 ± 0.19) |
| — (n = 10) | 3'-duGuo-5'-MP (50 mg/kg × 8) | 7.57 ± 0.64 | 9.83 ± 1.07 (1.30 ± 0.13) | 12.10 ± 2.00 (1.61 ± 0.27) | 15.40 ± 2.01 (2.05 ± 0.32) |
| araC (50 mg/kg × 8) (n = 10) | — | 7.49 ± 0.63 | 9.63 ± 0.68 (1.29 ± 0.13) | 11.91 ± 1.21 (1.60 ± 0.20) | 15.49 ± 1.26 (2.08 ± 0.20) |
| araC (50 mg/kg × 8) (n = 9) | 3'-dGuO-5'-MP (50 mg/kg × 8) | 7.34 ± 0.62 | 8.28 ± 1.11 (1.13 ± 0.15) | 9.12 ± 3.67 (1.26 ± 0.51) | 12.07 ± 4.98 (1.67 ± 0.68) |

EXPERIMENT 3

Acute toxicity test

The compounds of this invention were administered intraperitoneally to ICR mice (male, 8 weeks old, 10 mice for each group), and the mice were subjected to observation for a week.

The $LD_{50}$ value of 3'-dAdo-5'-MP was 500 mg/kg with confidence limit being 95% (417 to 600 mg/kg), and the $LD_{50}$ value of 3'-dGuo-5'-MP was estimated to be more than 1000 mg/kg. On the other hand, the $LD_{50}$ (i.p.) of 3'-dAdo was 280 mg/kg with confidence limit being 95% (241.4 to 324.8 mg/kg).

I claim:

1. A method of enhancement of anti-tumor effect which comprises administering to a tumor-bearing animal under an anti-tumor treatment an enhancer of the anti-tumor effect selected from the group consisting of 3'-deoxyguanosine-5'-monophosphate, 3'-deoxyadenosine-5'-monophosphate and pharmaceutically-acceptable salts thereof.

2. The method of enhancement of anti-tumor effect as claimed in claim 1 in which the anti-tumor treatment comprises irradiation of a tumor site of the animal and the enhancer is administered to the animal before, simultaneously with or after the irradiation.

3. The method of enhancement of anti-tumor effect as claimed in claim 2 in which the enhancer is administered to the animal before the animal is subjectd to the irradiation.

4. The method of enhancement of anti-tumor effect as claimed in claim 2 in which the enhancer is administered to the animal after the animal has been subjected to the irradiation.

5. The method of enhancement of anti-tumor effect as claimed in claim 1 in which the anti-tumor treatment comprises administration to the animal of an anti-tumor agent to the animal and the enhancer is administered to the animal before, simultaneously with or after the administration of the anti-tumor agent.

6. The method of enhancement of anti-tumor effect as claimed in claim 5 in which the anti-tumor agent is selected from the group consisting of anti-metabolites, anti-tumor antibiotics and alkylating agents.

7. In a method of treating tumor in a tumor-bearing animal, the improvement which comprises administering to a tumor-bearing animal under the anti-tumor treatment an enhancer of anti-tumor effect selected from the grop consisting of 3'-deoxyguanosine-5'-monophosphate, 3'-deoxyadenosine-5'-monophosphate and pharmaceutically-acceptable salts thereof.

8. The method of treating tumor as claimed in claim 7 in which the anti-tumor treatment comprises irradiation of a tumor site of the animal and the enhancer is administered to the animal before, simultaneously with or after the irradiation.

9. The method of treating tumor as claimed in claim 8 in which the enhancer is administered to the animal before the irradiation.

10. The method of treating tumor as claimed in claim 8 in which the enhancer is administered after the irradiation.

11. The method of treating tumor as claimed in claim 7 in which the anti-tumor treatment comprises administration to the animal of an anti-tumor agent and the enhancer is administered before, simultaneously with or after the administration of the anti-tumor agent.

12. The method of treating tumor as claimed in claim 11 in which the anti-tumor agent is selected from the group consisting of anti-metabolites, anti-tumor antibiotics and alkylating agents.

* * * * *